:

US008889194B2

(12) United States Patent
Bieley

(10) Patent No.: US 8,889,194 B2
(45) Date of Patent: Nov. 18, 2014

(54) SMOKING CESSATION WITH BODY WEIGHT MAINTENANCE AND NUTRITIONAL SUPPLEMENT

(76) Inventor: Harlan Clayton Bieley, West Palm Beach, FL (US)

( * ) Notice: Subject to any disclaimer, the term of this patent is extended or adjusted under 35 U.S.C. 154(b) by 712 days.

(21) Appl. No.: 12/893,910

(22) Filed: Sep. 29, 2010

(65) Prior Publication Data

US 2011/0014277 A1     Jan. 20, 2011

Related U.S. Application Data

(63) Continuation-in-part of application No. 11/969,199, filed on Jan. 3, 2008, now abandoned, and a continuation-in-part of application No. 12/571,391, filed on Sep. 30, 2009, now abandoned, said application No. 11/969,199 is a continuation-in-part of application No. 11/554,364, filed on Oct. 30, 2006, now abandoned, said application No. 12/571,691 is a continuation-in-part of application No. 11/554,364, filed on Oct. 30, 2006, now abandoned.

(60) Provisional application No. 60/951,328, filed on Jul. 23, 2007, provisional application No. 60/767,546, filed on Jun. 21, 2006.

(51) Int. Cl.

| A61K 31/07 | (2006.01) |
| A61K 31/14 | (2006.01) |
| A61K 31/198 | (2006.01) |
| A61K 31/32 | (2006.01) |
| A61K 31/355 | (2006.01) |
| A61K 31/375 | (2006.01) |
| A61K 31/4045 | (2006.01) |
| A61K 31/4188 | (2006.01) |
| A61K 31/519 | (2006.01) |
| A61K 31/525 | (2006.01) |
| A61K 31/59 | (2006.01) |
| A61K 31/675 | (2006.01) |
| A61K 38/43 | (2006.01) |
| A61K 31/714 | (2006.01) |
| A61P 25/30 | (2006.01) |
| A61K 45/06 | (2006.01) |
| A61K 31/137 | (2006.01) |
| A61K 31/22 | (2006.01) |
| A61K 31/7076 | (2006.01) |
| A61K 33/04 | (2006.01) |
| A61K 33/06 | (2006.01) |
| A61K 33/30 | (2006.01) |
| A61K 33/32 | (2006.01) |
| A61K 36/68 | (2006.01) |
| A61K 38/44 | (2006.01) |

(52) U.S. Cl.
CPC ............ *A61K 45/06* (2013.01); *A61K 31/07* (2013.01); *A61K 31/137* (2013.01); *A61K 31/14* (2013.01); *A61K 31/198* (2013.01); *A61K 31/22* (2013.01); *A61K 31/355* (2013.01); *A61K 31/375* (2013.01); *A61K 31/4045* (2013.01); *A61K 31/4188* (2013.01); *A61K 31/519* (2013.01); *A61K 31/525* (2013.01); *A61K 31/59* (2013.01); *A61K 31/675* (2013.01); *A61K 31/7076* (2013.01); *A61K 31/714* (2013.01); *A61K 33/04* (2013.01); *A61K 33/06* (2013.01); *A61K 33/30* (2013.01); *A61K 33/32* (2013.01); *A61K 36/68* (2013.01); *A61K 38/446* (2013.01); *C12Y 115/01001* (2013.01)
USPC ............ 424/600; 514/387; 514/52; 514/419; 514/654; 514/415; 514/642; 514/458; 514/546; 514/251; 514/725; 514/474; 514/167; 514/21.9; 514/249

(58) Field of Classification Search
USPC ........... 514/387, 52, 419, 654, 415, 642, 458, 514/546, 251, 725, 474, 167, 21.9, 249; 424/600
See application file for complete search history.

(56) References Cited

U.S. PATENT DOCUMENTS

| 4,596,706 A | 6/1986 | Revici |
| 5,573,774 A | 11/1996 | Keenan |
| 5,599,554 A | 2/1997 | Majeti |
| 5,614,523 A | 3/1997 | Audia et al. |
| 5,643,928 A | 7/1997 | Keenan |

(Continued)

FOREIGN PATENT DOCUMENTS

| EP | 1 304 048 | 4/2003 |
| WO | WO-01/26642 | 4/2001 |
| WO | WO 01/26642 A2 * | 4/2001 |

OTHER PUBLICATIONS

International Search Report dated Jun. 16, 2011 from PCT/US2010/050774.

*Primary Examiner* — Sreeni Padmanabhan
*Assistant Examiner* — Sahar Javanmard
(74) *Attorney, Agent, or Firm* — Foley Hoag LLP

(57) ABSTRACT

Disclosed is a compound and methods for use by an individual attempting to reduce or cease tobacco smoking or one exposed to environmental tobacco smoke. The compound includes a first component blocking nicotine receptor sites to reduce nicotine cravings or withdrawal symptoms, a second component increasing serotonin levels and acting synergistically with the first component to reduce nicotine cravings or withdrawal symptoms, assisting in maintaining body weight and reducing increased stress and anxiety, and a third component acting synergistically with the first and/or second component to reduce nicotine cravings or withdrawal symptoms, maintain body weight, and/or reduce increased stress and anxiety. The third component comprises a supplement that replenishes depleted body substance(s), repairs damaged body substance(s), and/or ameliorates the impaired function of body substance(s). Some combination of the first, second, and third component alters the perceived taste of tobacco smoke.

4 Claims, 4 Drawing Sheets

(56) References Cited

U.S. PATENT DOCUMENTS

| | | |
|---|---|---|
| 5,747,512 A | 5/1998 | Keenan et al. |
| 5,760,049 A | 6/1998 | Viner |
| 5,852,032 A | 12/1998 | Mason |
| 5,869,503 A | 2/1999 | Keenan |
| 5,869,505 A | 2/1999 | Keenan |
| 5,922,346 A | 7/1999 | Hersh |
| 5,972,974 A | 10/1999 | Keenan |
| 6,166,032 A | 12/2000 | Viner |
| 6,409,991 B1 | 6/2002 | Reynolds |
| 6,431,874 B1 | 8/2002 | Szynalski |
| 6,541,478 B1 | 4/2003 | O'Malley et al. |
| 6,541,520 B1 | 4/2003 | Dewey et al. |
| 6,645,470 B1 | 11/2003 | Reynolds |
| 6,828,349 B1 | 12/2004 | Dewey et al. |
| 2003/0176358 A1 | 9/2003 | Egawa et al. |
| 2005/0274391 A1* | 12/2005 | Groke et al. ............ 131/359 |

* cited by examiner

SMOKING CESSATION WITH BODY WEIGHT MAINTENANCE AND NUTRITIONAL SUPPLEMENT

CROSS-REFERENCE TO RELATED APPLICATIONS

The present application is a continuation-in-part of abandoned U.S. patent application Ser. No. 11/969,199 filed Jan. 3, 2008 for REPLACEMENT OF VITAMINS, MINERALS AND NEUROTRANSMITTER LOSSES FROM TOBACCO SMOKE based on expired U.S. Provisional Patent Application Ser. Nos. 60/767,546 filed Jun. 21, 2006 and 60/951,328 filed Jul. 23, 2007; and a continuation-in-part of abandoned U.S. patent application Ser. No. 12/571,391 filed Sep. 30, 2009 for SMOKING CESSATION TREATMENT BY REDUCING NICOTINE CRAVINGS, APPETITE SUPPRESSION, AND ALTERING THE PERCEIVED TASTE OF TOBACCO SMOKE; both of which are continuations-in-part of abandoned U.S. patent application Ser. No. 11/554,364 filed Oct. 30, 2006 for SMOKING CESSATION TREATMENT WITH APPETITE SUPPRESSION, which was based on expired U.S. Provisional Patent Application Ser. No. 60/767,546 filed Jun. 21, 2006. Each of these applications is hereby fully incorporated by reference for all that is disclosed therein.

BACKGROUND

There are numerous health problems associated with tobacco smoking. In addition to the presence of highly-addictive nicotine, tobacco products contain thousands of chemical compounds and additives, many of which are known carcinogens. In addition, tobacco smoke contains heavy metals such as lead and cadmium. Cadmium causes the depletion of zinc and Vitamin D and can also interfere with the metabolism of Vitamin D. In addition, the body stores cadmium in fat and may retain it for a substantial amount of time. Tobacco smoke also specifically contains carbon monoxide, nitrogen oxide, hydrogen cyanide and ammonia, all of which are toxic and/or carcinogenic to an individual. Tobacco smoking, and in particular cigarette smoking, is responsible for the majority of lung cancers and is also associated with cancers of the mouth, pharynx, larynx, esophagus, stomach, pancreas, uterine cervix, kidney, ureter, bladder and colon, as well as leukemia. In addition to the carcinogenic effects of tobacco smoking, such activity is believed to increase risk of cardiovascular diseases (including stroke), sudden death, cardiac arrest, peripheral vascular disease, and aortic aneurysm. Furthermore, many components of tobacco smoke have been characterized as ciliotoxic materials that irritate the lining of the respiratory system resulting in increased bronchial mucus secretion and chronic decreases in pulmonary and mucociliary function.

Smokers and non-smokers may also be exposed to environmental tobacco smoke, which is produced by inhalation of tobacco smoke by a smoker and then exhalation thereof into the environment (mainstream tobacco smoke) or emitted by a burning tobacco-containing product such as a cigarette (sidestream tobacco smoke). Whereas the chemical compositions of mainstream smoke and sidestream tobacco smoke are qualitatively similar since they are both derived from burning tobacco, there are some significant quantitative differences between the two types of smoke. In particular, since the smoker is actively inhaling from a tobacco-containing product during the initial generation of mainstream smoke, the temperature at which mainstream tobacco smoke is formed is much higher than the temperature at which sidestream tobacco smoke is formed. As a result, sidestream tobacco smoke which pervades the environment of a smoker contains larger quantities of many chemical compounds as compared to mainstream tobacco smoke, which suggests that sidestream smoke is even more carcinogenic than mainstream tobacco smoke. Thus, those exposed to environmental tobacco smoke are at considerable risk for health problems. Those exposed to environmental tobacco smoke include not only the smokers themselves, but also non-smokers in the general vicinity of smokers, in particular, children, spouses, other family members and friends of smokers.

In a tobacco product such as a cigarette, tobacco and its additives are not the only part of the product that carries dangerous chemicals. In particular, the paper used by cigarette manufacturers may be engineered to burn slowly. This can be accomplished, among other ways, by the addition of antimony to the paper. Whereas the addition of antimony makes the paper burn slowly, it could also places another toxic material, antimony, into the smoker's body and the environment.

In addition to the carcinogenic and other health problems described above that are associated with smoking tobacco, smoking tobacco also impacts the body's ability to function normally by interfering with important body resources. In particular, body substances such as, for example, vitamins, minerals, enzymes, amino acids, cofactors, precursors, neurotransmitters, cellular constituents, and the like are depleted, damaged, or interfered with in an individual directly as a result of smoking tobacco products and being exposed to environmental tobacco smoke. Such depletion of, damage of, or interference with vital body substances can result in a variety of health problems and/or increase the risk for the health problems described above for smokers and those exposed to environmental tobacco smoke.

Because of such health risks and problems for smokers and those exposed to environmental tobacco smoke, many individuals attempt to cease smoking tobacco or at least reduce the amount of tobacco smoked on a daily basis. For many reasons, reducing or ceasing smoking tobacco is a very difficult process. First, as noted above, nicotine is highly addictive. Individuals attempting to cease smoking tobacco often fail due to the nicotine cravings and withdrawal symptoms they experience. Second, many individuals are attracted to smoking tobacco by its taste, which has been described as somewhat bitter but pleasant. Much of the bitter taste comes from nicotine itself. However, additives including menthol and other flavors are included in tobacco products to enhance the taste of their product or appeal to the tastes of different individuals (e.g., those who prefer menthol cigarettes as opposed to regular ones). The ability to sense the bitter taste of nicotine as well as possibly the added taste enhancers in tobacco smoke are important components for the desire to smoke tobacco. Third, constantly drawing on willpower to reduce or cease what may be a long-term habit of smoking tobacco and experiencing nicotine cravings and withdrawal symptoms can create secondary problems related to smoking, such as an increase in stress and anxiety resulting in an increase in appetite. Such an increase in appetite can result in undesirable increases in body weight, which, in turn, can result in even more health problems as well as an unattractive change in the individual's appearance. The undesirable increases in body weight in itself can also have a detrimental effect on an individual's willpower to reduce or cease smoking tobacco. Each of these effects, any of the effects in combination, and especially all of the effects in combination, can be detrimental to an individual attempting to reduce or cease smoking tobacco.

Smoking cessation products have typically attempted to reduce nicotine cravings and withdrawal symptoms in several ways. One method has been the use of nicotine-containing substances such as transdermal patches or chewing gum which permit individuals to satisfy the body's cravings for nicotine without damaging their lungs by inhaling tobacco smoke. Whereas such products temporarily assist in reducing nicotine cravings and withdrawal symptoms, they do nothing to overcome an individual's addiction to nicotine since their effects cease once the patch is removed or the chewing gum is discarded. Such products also do nothing to address the other effects discussed above that are associated with reducing or ceasing smoking tobacco. Other smoking cessation products that do not use nicotine-containing substances include chemical substances that bind to specific cell receptor sites in the brain, thus preventing nicotine from binding to those cell receptor sites which assists in controlling nicotine cravings and withdrawal symptoms. Such products typically contain bivalent negative sulfur compounds such as alkyl sulfides, colloidal sulfur, hydropersulfides, organic thio compounds or their salts. Whereas such products may gradually assist in reducing nicotine cravings and withdrawal symptoms, they do nothing to overcome the other effects discussed above that are associated with reducing or ceasing smoking tobacco. Furthermore, none of the smoking cessation products noted above do anything to overcome the health problems due to environmental smoke, which affect both smokers and non-smokers in the general vicinity of smokers, in particular, children, spouses, other family members and friends of smokers.

DETAILED DESCRIPTION

Figure 1:
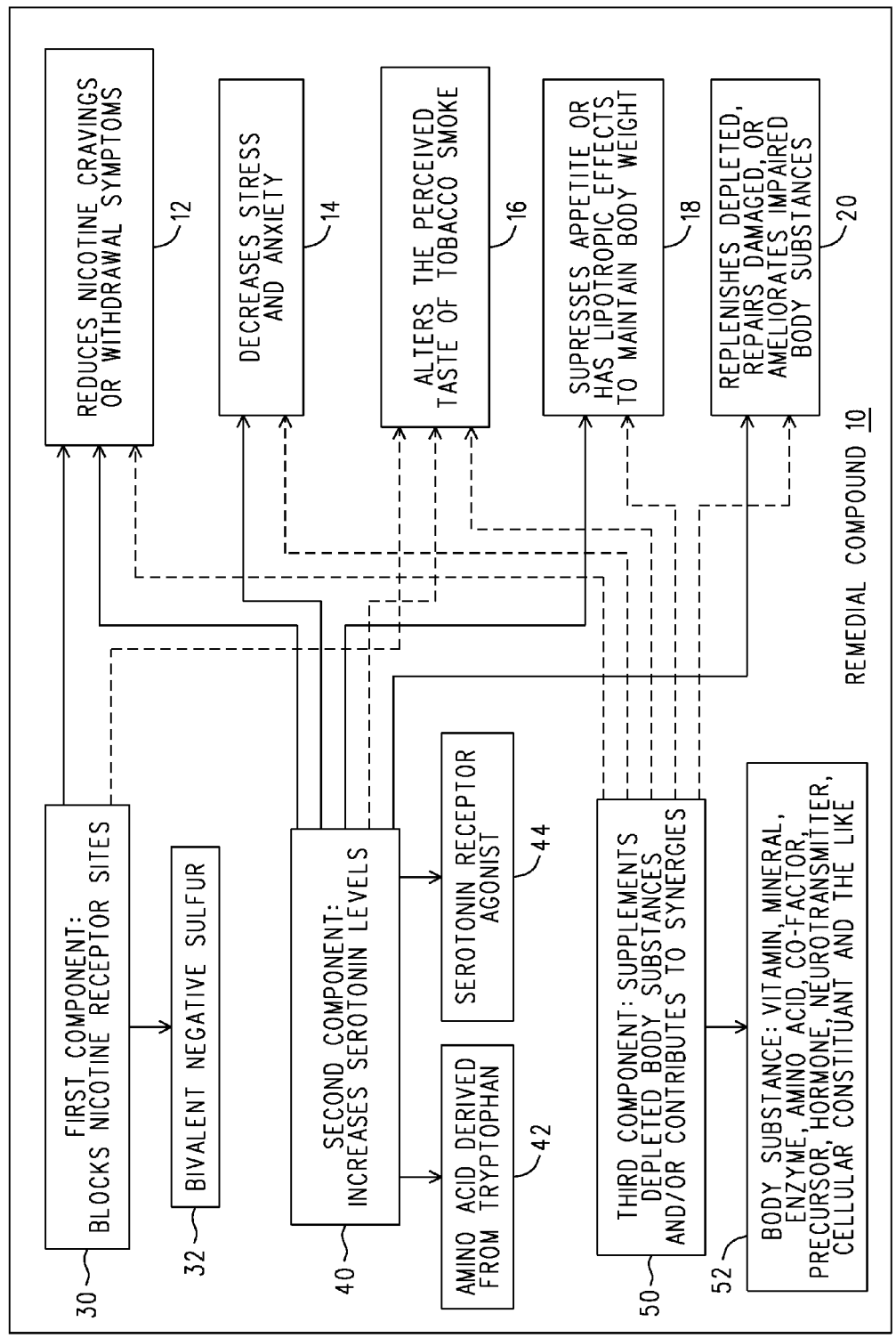
FIG. 1 is a schematic illustration of a remedial compound and its synergistic effects.

The drawings and description, in general, provide a system comprising a remedial compound 10, FIG. 1, that synergistically reduces nicotine cravings or withdrawal symptoms 12 to assist an individual in ceasing smoking tobacco or at least reducing the amount of tobacco smoked on a daily basis, decreases stress and anxiety 14 in an individual attempting to cease or reduce smoking tobacco, alters the perceived taste of tobacco smoke 16 to deter continued smoking of tobacco, and suppresses the individual's appetite or has lipotropic effects to allow maintenance (including possibly loss) of body weight 18. Whereas suppressing appetite avoids undesirable side effects from reducing or quitting smoking such as increased appetite and consequential weight gain, elements that have lipotropic effects enhance the body's ability of metabolize fat, thereby maintaining body weight (which includes suppressing the gain of body weight as well as losing body weight) while reducing or quitting smoking. Also provided is a nutritional supplement that replenishes depleted body substances 20, repairs damaged body substances 20, or ameliorates the function of body substances 20 that are impaired as a direct result of smoking tobacco or being exposed to environmental tobacco smoke. Such body substances may include vitamins, minerals, enzymes, amino acids, cofactors, precursors, hormones, neurotransmitters, cellular constituents, and the like that are depleted, damaged, or impaired as a consequence of smoking tobacco or of being exposed to tobacco smoke in the environment (i.e., "second-hand" smoke). As indicated by dashed lines, at least some of the elements in the nutritional supplement contribute to one or more of the above-described synergistic effects 12, 14, 16, 18 as well. Also provided is a method of replenishing body substances, repairing body substances, or ameliorating the function of body substances that are depleted, damaged or impaired in an individual as a direct result of smoking tobacco or being exposed to environmental tobacco smoke. Further provided is a method of assisting an individual attempting to reduce or cease tobacco smoking by administering a compound that acts synergistically on the effects 12, 14, 16, 18 described herein.

The phrase "remedial" is used herein to define a remedy that is utilized, for example, to relieve a bodily disorder or restore an imbalance of one or more body substances to healthier or optimal conditions. The phrase "smoking tobacco" includes any means of inhaling and exhaling nicotine-containing tobacco smoke into and out of an individual's oral cavities and lungs such as via cigarettes, pipes, or the like. Also discussed herein is the effect of being exposed to tobacco smoke that is present in the environment, or "second-hand" smoke, as would be experienced by, for example, a non-smoking household member of a smoker. The word "synergy" and its derivatives, as used in the present application, is defined as the interaction of two or more components to produce results that, in combination, are different, additive, and may often be greater than the expected or anticipated effect of each element utilized separately and individually. In many cases, the synergistic behavior of such combined components or forces as a system has a novel effect unpredictable and unanticipated by the behavior of any individual component taken separately from the system.

As illustrated in FIG. 1, the first component 30 of the compound 10 comprises at least one element that blocks nicotine receptor sites in the human body in an amount sufficient to assist in controlling cravings or withdrawal symptoms within an individual attempting to quit smoking tobacco resulting from deprivation of nicotine from that individual's body. An example of such an element is bivalent negative sulfur 32 which may be selected from a group that includes, but is not limited to, Hydropersulfides, Alkyl sulfides, Colloidal sulfur, organic Thio compounds or their pharmaceutically acceptable salts. Presently preferred Thio compounds include Thioglycerols, Thioglycols, and their pharmaceutically acceptable salts.

The second component 40 of the compound 10 comprises at least one element that increases serotonin levels in the human body such as, for example, amino acids derived from tryptophan 42 and, more specifically, 5-hydroxytryptophan (5-HTP) or related tryptophan derivatives, in an amount sufficient to assist in suppressing an individual's appetite, assist in reducing cravings for nicotine or withdrawal symptoms, and assist in reducing stress and anxiety in an individual attempting to cease or reduce smoking tobacco. Smoking tobacco has also been shown to decrease the levels of serotonin in an individual, and this effect could also be present in an individual exposed to environmental smoke. Thus, the second component of the compound also replenishes the depleted serotonin in such an individual's body.

Whereas 5-HTP can be derived from the amino acid L-tryptophan as noted above, it can also be derived from *Griffonia simplicifolia* seed extract or other sources. Tryptophan, including L-tryptophan and its derivatives, plays a vital role in our health in that it is an essential amino acid utilized by the human body for building proteins and enzymes, as well as serving as a precursor, along with cofactor tetrahydrobiopterin, to serotonin (5-hydroxytryptamine or 5-HT) and the hydrogen carriers NADH and NADPH. Serotonin is a neurotransmitter that plays an important role in regulation of mood, appetite, body temperature, and the secretion of various hormones, and serotonin levels may be depleted in cigarette smokers and those exposed to environmental smoke. Whereas serotonin does not readily cross the blood brain barrier, serotonin precursors such as 5-HTP and L-tryptophan can cross the blood brain barrier. As a result, ingesting 5-HTP, L-tryptophan or related tryptophan derivatives increases levels of serotonin in the body. Whereas L-tryptophan and other such derivatives are appropriate for use in the second component of the compound, 5-HTP is generally more efficient in the human body than L-tryptophan because 5-HTP bypasses the rate-limiting step of serotonin synthesis which utilizes the enzyme tryptophan hydroxylase.

Tryptophan, including 5-HTP, L-tryptophan, and the like, has a variety of positive side effects when ingested by humans. For example, tryptophan can be used as a mood- and sleep-enhancer and is commonly used to treat depression and insomnia, thus playing a synergistic role in reducing stress and anxiety in individuals attempting to quit smoking tobacco. Tryptophan can also increase pain tolerance and reduce appetite, in particular cravings for certain carbohydrates. Furthermore, as compared to other, conventional appetite suppressants, 5-HTP has a relatively small molecule size, thus allowing 5-HTP access to the brain through the bloodstream. Once in the brain, 5-HTP can be converted into serotonin, which acts on the different serotonin receptor sites in order to suppress an individual's appetite as well as helps reduce cravings for nicotine or withdrawal symptoms in an individual attempting to reduce or cease smoking tobacco. Also, as compared to other appetite suppressants, 5-HTP is a naturally occurring element that is produced in the body from tryptophan and can be found in high-protein foods such as beef, chicken, fish, and dairy products. Thus, supplementing an individual's body with 5-HTP for appetite suppression is relatively safer than utilizing non-naturally-occurring ingredients found in some conventional appetite suppressants.

Because tryptophan (including its derivatives such as, for example, 5-HTP) is a precursor used by the body to produce serotonin, its use in combination with the aforementioned first component of the compound that blocks nicotine receptor sites allows an individual to improve the chances of successfully and less painfully overcoming a tobacco smoking habit. For example, because serotonin also inhibits nicotine cravings and withdrawal symptoms, the second component that increases serotonin levels in an individual acts synergistically with the first component that blocks nicotine receptor sites in order to significantly reduce nicotine cravings and withdrawal symptoms in an individual ingesting a compound containing both the first and second components.

One or more serotonin receptor agonists 44 may also or alternatively be utilized as the second component 40 of the compound 10 in order to increase serotonin levels in the human body. Such serotonin receptor agonists activate serotonin receptors, mimicking the effect of the neurotransmitter serotonin in the human body. Examples of serotonin receptor agonists include, but are not limited to, selective 5-HT receptor agonists such as Azapirones (e.g., Buspirone and the like) which is an agonist to the 5-HT1A receptor sites, Triptans (e.g., Sumatriptan and the like) which are agonists to the 5-HT1B and 5-HT1D receptor sites, Lasmiditan which is an agonist to the 5-HT1F receptor sites, Trazodone which is an agonist to the 5-HT2 receptor sites, Lorcaserin which is an agonist to the 5-HT2C receptor sites, and Cisapride which is agonist to the 5-HT4 receptor sites. Another example of serotonin receptor agonists include, but are not limited to, non-selective 5-HT receptor agonists such as Ergotamine which is an agonist to the 5-HT1A, 5-HT1D, 5-HT1B, D2, and norepinephrine receptor sites; and psychedelic drugs (LSD, mescaline, and the like) which is an agonist at least to the 5-HT2A receptor sites. There are many other serotonin receptor agonists not listed above, and these examples are not intended to be an exhaustive list of such agonists.

A third component 50 of the compound 10 comprises a supplement that replenishes depleted body substances 20, repairs damaged body substances 20, or restores function of body substances 20 that are depleted, damaged, or their function impaired as a direct result of smoking or as a result of being exposed to environmental tobacco smoke. The third component 50 of the compound 10 may also contribute to one or more of the synergies described above related to reducing nicotine cravings or withdrawal symptoms 12, decreasing stress and anxiety 14, altering the perceived taste of tobacco smoke 16, and maintaining body weight 18 in an individual attempting to reduce or cease smoking tobacco. In particular, the supplement consists of one or more body substances 52 which may be vitamins, minerals, enzymes, amino acids, cofactors, precursors, hormones, neurotransmitters, cellular constituents, and the like. The supplement may consist of the following in any of their forms (some specific examples of these forms being given below): Alpha lipoic acid; Chromium in any of its forms including Chromium picolinate; Biotin; Tyrosine in any of its forms including N-acetyl tyrosine; Tetrahydrobiopterin which is a cofactor; L-phenylalanine and/or DL-phenylalanine; *Gymnema sylvestre* (Gumar); Arginine; Green tea with Epigallocatechin gallate (EGCG); Butyrate in any of its forms including Sodium butyrate, sodium potassium butyrate, and calcium magnesium butyrate; *Mucuna puriens* (Cowage seed); Magnesium in any of its forms including Magnesium glycinate, Magnesium malate, Magnesium taurate, and Magnesium citrate; N-acetylcysteine and/or Glutathione (which can be made by N-acetylcysteine); L-theanine; *Magnolia officianalis*; Taurine; Melatonin (a hormone and an antioxidant); Vitamin B-6 in any of its forms, activated and/or unactivated, including Pyridoxal-5-phosphate and Pyridoxine hydrochloride; Inositol; Vinpocetin; Glycine; Niacinamide; Valerian Root; Kava kava; Phosphatidylserine; *Bacopa monnieri; Rhodiola rosea*; Holy basil; Ashwagandha; Vitamin C (buffered or in any other form); Vitamin B-12 in any of its forms including Methylcobalamin, Cyanocobalamin, and Hydroxocobalamin; Choline in any of its forms including Phosphatidylcholine and Choline citrate; Methionine in any of its forms including L-methionine; S-adenosylmethionine (SAM-e); Calcium; Vitamin E in any of its forms including Tocopherols and Tocotrienols such as Alpha tocopherol and Gamma tocoperhol; Folate in any of its forms including Folic acid, Folinic acid, L-methylfolate, and 5-methyl tetrahydrofolate; Manganese; Vitamin B2 in any of its forms including Riboflavin-5-phosphate; Vitamin A; Selenium in any of its forms including Selenomethionine; Zinc in any of its forms including Zinc glycinate, Zinc picolinate, and/or Zinc citrate; Carotenoid in any of its forms including Alpha-carotene, Beta-carotene, Beta-cryptoxanthin, Zeaxanthin, Lycopene and Lutein; Bioflavonoid and/or any element that increases a Bioflavonoid including Quercetin, Hesperidin, Garlic, and Pycnogenol; Vitamin D in any of its forms including Vitamin D3 (which is a vitamin and acts as a hormone); CoQ10; GABA, a GABA agonist (direct or indirect), and/or an element that binds to GABA receptors (some of which have been included above); serotonin, a serotonin agonist (direct or indirect), and/or an element that binds to serotonin receptors (some of which have been included above); dopamine, a dopamine agonist (direct or indirect), and/or an element that binds to dopamine receptors (some of which have been included above).

Figure 3:
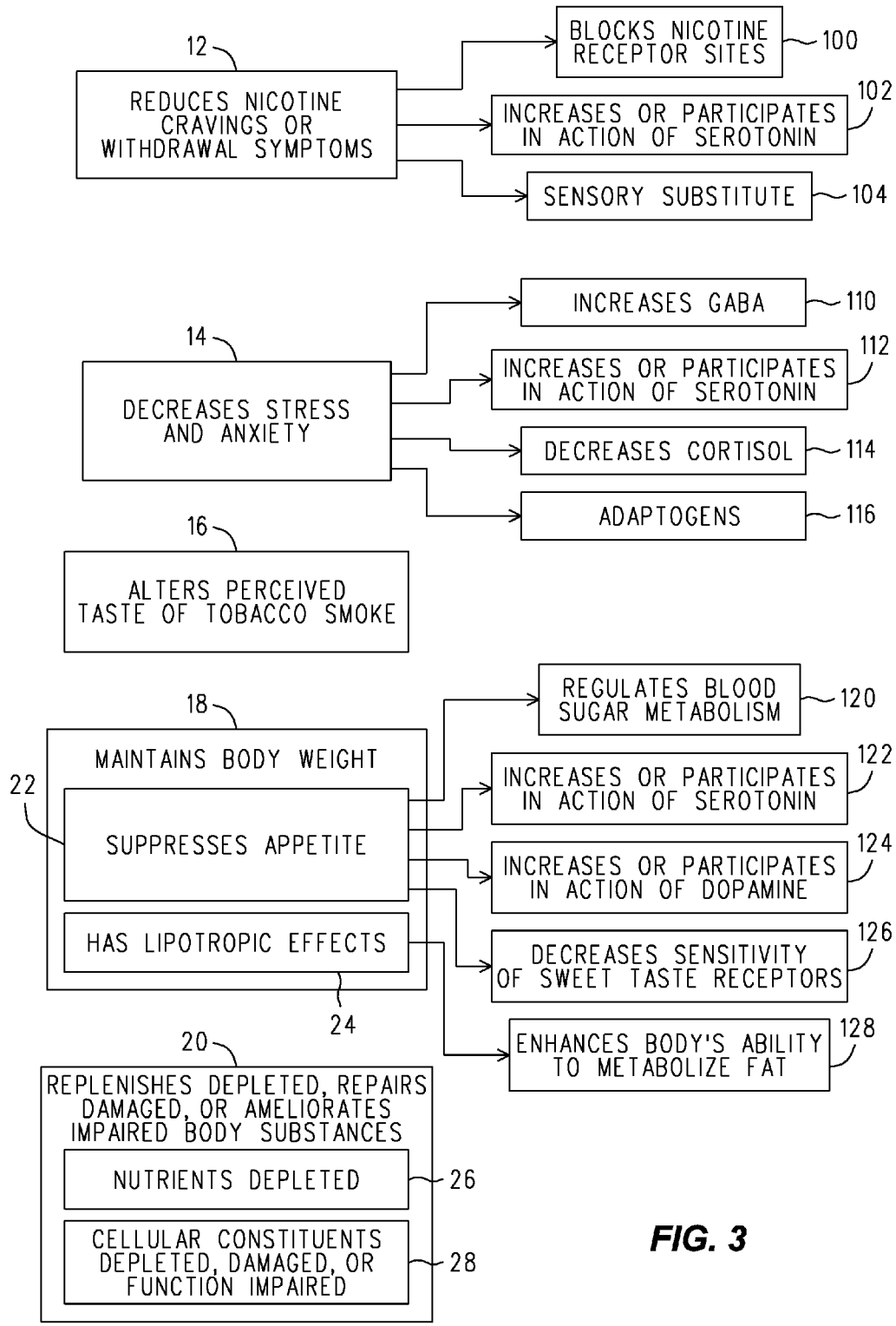
FIG. 3 is a schematic illustration of the synergistic effects of FIG. 1 and the manners in which such effects can be achieved.

FIG. 3 illustrates the synergistic effects 12, 14, 16, 18, 20 noted above with reference to FIG. 1 and the manners in which such effects can be achieved. As illustrated in FIG. 3, nicotine cravings or withdrawal symptoms can be reduced 12 by any of the following: an element 100 that blocks nicotine receptor sites, an element 102 that increases serotonin levels or participates in the action of serotonin, or a sensory substitute 104. As explained above, the first component 30, FIG. 1, of the compound 10 which is a bivalent negative sulfur 32 blocks nicotine receptor sites 100, FIG. 3. An element 102 that increases serotonin levels is the second component 40, FIG. 1, of the compound 10 such as 5-HTP, which is a serotonin precursor. Other elements 102 that increase serotonin levels or participate in the action of serotonin include Magnesium, which prolongs the effects of 5-HTP; Inositol, which acts on receptors linked to serotonin signaling; Vinpocetin, which directly raises serotonin levels; and S-adenosylmethionine (SAMe) which augments serotonin reuptake inhibitors. An element 104 that acts as a sensory substitute is Vitamin C. As a sensory substitute, Vitamin C (specifically as ascorbic acid) has been shown to enhance smoking reduction by reducing nicotine cravings or withdrawal symptoms.

Also as indicated in FIG. 3, stress and anxiety may be decreased 14 by utilizing an element 110 that increases GABA or participate the action of GABA. In particular, GABA, GABA agonists, and other elements that increase GABA generally help reduce stress and anxiety in an individual and thus may also be utilized synergistically with the first and second components as well as other elements of the third component of the compound to help reduce stress and anxiety in an individual attempting to reduce or cease smoking tobacco. For example, L-theanine and N-acetylcysteine do not directly increase GABA, but instead are GABA modulators that dampens glutamate. Thus, L-theanine is a glutamate antagonist and also acts to increase dopamine levels and decrease Norepinephrine levels which results in reduced stress and anxiety in an individual. As another example, *Magnolia officianalis* works on the GABA A site to reduce anxiety, and also works on the Adenosine A1 sites which can lower stress and anxiety. Other GABA agonists (direct or indirect) include Magnesium, Vitamin B6, Inositol, Taurine, and Melatonin (which increases GABA and Taurine). Alpha lipoic acid increases PGC1-alpha which increases GABA. Elements that bind to GABA receptors and directly increase GABA include Glycine, Niacinamide, Valerian root, Kava kava, and green tea with Epigallocatechin gallate (EGCG).

Stress and anxiety may also be decreased 14 by utilizing an element 112, FIG. 3, that increases or participates in the action of serotonin. Not only does increasing serotonin decrease nicotine cravings and withdrawal symptoms, but it also decreases stress and anxiety. Thus, as noted above, an element 112 that increases serotonin levels is the second component 40, FIG. 1, of the compound 10 that increases serotonin such as 5-HTP, which is a serotonin precursor. Other elements 112 that increase serotonin levels or participate in the action of serotonin include Magnesium, which prolongs the effects of 5-HTP; Inositol, which acts on receptors linked to serotonin signaling; Vinpocetin, which directly raises serotonin levels; and S-adenosylmethionine (SAMe), which augments serotonin reuptake inhibitors.

Another way to decrease stress and anxiety 14 is by utilizing an element 114, FIG. 3, that decreases cortisol. One such element is Phosphatidylserine. Adaptogens 116 help the body adapt to stress, support normal functions, and restore balance and thus act to decrease stress and anxiety 14. Such adaptogens include *Bacopa monnieri, Rhodiola rosea*, Holy basil, and Ashwagandha.

At least one of the first, second and third components 30, 40, 50 (or possibly some combination of the first, second and third components 30, 40, 50) also appears to alter the perceived taste of tobacco smoke 16, FIGS. 1 and 3. Whereas the specific effect regarding taste may vary among individuals, an observed effect as a result of an individual ingesting some combination of the first, second and/or third components 30, 40, 50 has been an enhancement of the certain taste receptors 62 on upper side 64 the tongue 60, FIG. 2, in regions 70 on the tongue 60 that detect sourness located generally at the right and left sides 80, 82 of the tongue 60, thus making tobacco smoke taste "sour" to the individual. Other taste receptors, those on the tongue 60 (generally illustrated as 62 in FIG. 2) as well as the palate and/or pharynx (not shown), may be affected as well, by enhancing or lowering the sensitivity of different taste receptors. These other taste receptors may be in a region 72 that detects sweetness (a region that partially overlaps the sour regions 70) at the front (e.g., tip) 84 of the tongue 60, a region 74 that detects bitterness toward the rear 86 of the tongue 60, and a region 76 that detects saltiness (notably a region that partially overlaps each of the other regions 70, 72, 74) around the edges 88 of the tongue 60. The souring effect has also been observed to increase with continued ingestion of the first, second and/or third components 30, 40, 50, e.g., letting the component(s) build up in the individual's bloodstream. Other individuals who have ingested some combination of the first, second, and/or third components 30, 40, 50 have noted an "unpleasant bitter" taste (which may be due to an enhancement of taste receptors 62 that detect sourness as well) when smoking tobacco. Again, this effect has been observed to increase with continued ingestion of the first and second components together. Regardless of the specific description of the taste, the taste of tobacco smoke that is altered by ingesting the first, second, and/or third components, or some combination thereof, can be consistently and generically described as "unpleasant" such that the individual is discouraged from smoking due to the unpleasantness of the taste of the smoke. This unexpected result is achieved through the synergistic interaction among some combination of the first, second and/or third components within an individual's body, and may be enhanced and/or exacerbated with the continued ingestion of these components.

As illustrated in FIG. 3, certain elements suppress appetite 22 or have lipotropic effects 24, thus maintaining body weight 18 (either by suppressing body weight gain or causing loss of body weight) in an individual attempting to reduce or cease smoking tobacco. Suppressing appetite 22 can be achieved by regulating blood sugar metabolism 120, thereby decreasing appetite 22 since cravings for certain carbohydrates such as sugars are decreased. Alpha lipoic acid is such an element that improves blood sugar metabolism 120 in that it stimulates uptake of glucose via stimulation of GLUT 4 protein, which is a primary glucose transporter in muscle, cardiac and fat cells. Alpha lipoic acid is also an up-regulator cofactor for insulin, thyroid, GABA, and other catecholamines. Chromium, in particular Chromium picolinate, acts synergistically with Biotin to regulate blood sugar metabolism 120 by improving glucose tolerance, thus suppressing appetite 22. Butyrate and *Gymnema sylvestre* (Gumar) also regulate blood sugar metabolism 120 through increased insulin sensitivity.

Figure 2:
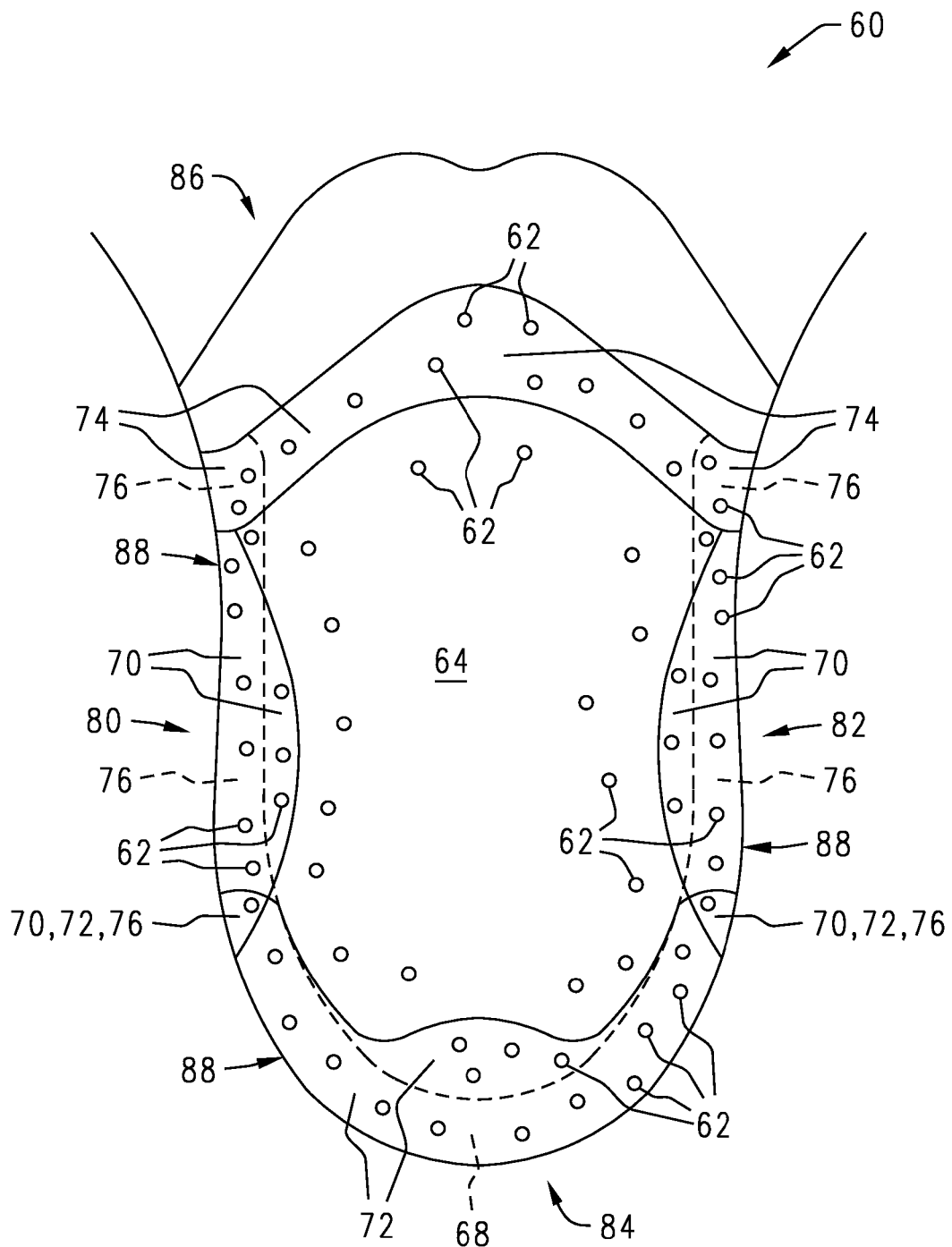
FIG. 2 is a top view of a tongue generally illustrating taste receptor areas.

Suppressing appetite 22 can also be achieved by increasing or participating in the action of serotonin 122, which have been described above and include second component 40, FIG. 1, of the compound 10 such as 5-HTP, which is a serotonin precursor; Magnesium, which prolongs the effects of 5-HTP; Inositol, which acts on receptors linked to serotonin signaling; Vinpocetin, which directly raises serotonin levels; and S-adenosylmethionine (SAMe), which augments serotonin reuptake inhibitors. Suppressing appetite 22 can further be achieved by increasing or participating in the action of dopamine 124. 5-HTP not only increases serotonin, but it also increases dopamine and norepinephrine, all of which decrease cravings for certain carbohydrates. Tyrosine and its derivatives increase dopamine by being converted, with Tetrahydrobiopterin as a cofactor, within the body to the catecholamine neurotransmitters (dopamine, norepinephrine, and epinephrine), all of which decrease cravings for certain carbohydrates. L-phenylalanine and/or DL-phenylalanine also increase dopamine as well as norepinephrine. Arginine increases dopamine since it is a dopamine agonist. Green tea with Epigallocatechin gallate (EGCG) augments dopamine, and *Mucuna puriens* (Cowage seed) contains naturally-occurring levodopa (L-Dopa), which is an intermediate in dopamine synthesis. *Gymnema sylvestre* (Gumar), as well as regulating blood sugar metabolism as described above, also suppresses appetite 22 by decreasing the sensitivity of taste receptors that detect sweetness 126, which decreases the desire for sweet foods including those containing sugars. As shown in FIG. 2, at least some of the sweetness taste receptors are located at the tip 84 of the tongue 60 as indicated at 72.

As indicated in FIG. 3, elements that have lipotropic effects 24 can also allow an individual attempting to reduce or cease smoking to maintain body weight 18 by enhancing the body's ability of metabolize fat 128. Such elements 128 include Vitamin B6, Vitamin B12, Choline (including Phosphatidylcholine and other forms of Choline), Inositol, Methionine, and S-adenosylmethionine (SAMe). Methionine and SAMe are each used in the methionine/methylation cycle which activates serotonin and melatonin production.

A supplement that replenishes depleted body substances 20, repairs damaged body substances 20, or ameliorates the function of body substances 20 may include nutrients that are depleted 26 from an individual's body as well as cellular constituents such as, for example, enzymes and cofactors that are depleted, damaged, or their function impaired 28 due to smoking tobacco or being exposed to environmental tobacco smoke. Nutrients that are depleted 26 from an individual's body include (in any of their forms noted above) Vitamin B6, Biotin, Vitamin B12, Melatonin, Dopamine, Serotonin, Choline, Calcium, Vitamin E, Folate, Magnesium, Manganese, Vitamin B2, Vitamin A, Vitamin C, Selenium, Zinc, Carotenoids, Bioflavonoids, Vitamin D, Glutathione (which can be made from N-acetylcysteine), and S-adenosylmethionine (SAMe). Cellular constituents that are depleted, damaged, or their function impaired 28 include vascular endothelium which can be improved by CoQ10 and Melatonin, Catalase, which can be increased by Bacopa; Glutathione reductase and Glutathione peroxidase, which can be increased by N-acetylcysteine; Sulfhydryl moiety, which is critical for enzyme function; Superoxide dismutase; and Peroxisomal enzyme (alkyl DHAP), which can be increased by Butyrate.

Choline, and in particular Phosphatidylcholine, maintains and reestablishes cellular membranes which may be lost or damaged due to tobacco smoking or exposure to second-hand tobacco smoke. This element does so by increasing polyunsaturated fats in the cell membrane, thereby helping to restore the cell membrane. CoQ10 helps repair and rebuild vascular endothelium and other cellular constituents damaged by tobacco smoking. Melatonin reduces vasoconstriction and oxidative stress and improves endothelial physiology.

Exemplary ranges for a daily dosage of each of the above-described elements will now be listed. These ranges are not intended to be limiting, and the daily dosage of any of these elements may depend on such factors as the amount of exposure to tobacco smoke for smokers and those exposed to environmental smoke including daily amount and total amount of exposure, body weight, age, biochemical sensitivity and uniqueness, physical condition, severity of withdrawal symptoms, and the like. Thus, the element and amount thereof given can be changed to suit an individual's unique biochemical diversity. The exemplary daily dosage ranges are as follows, in any form including those stated above:

1. 25-900 mg 5-HTP or other amino acids derived from tryptophan
2. 25-750 mg Thioglycerol or other bivalent negative sulfur
3. 25-1,600 mg Alpha lipoic acid
4. 10-1,600 mcg Chromium
5. 10 mcg-10 mg Biotin
6. 10-4,000 mg Tyrosine
7. 20-1,400 mg Tetrahydrobiopterin (a cofactor for Tryptophan and Tyrosine)
8. 10-4,000 mg L-phenylalanine and/or DL-phenylalanine in any combination
9. 10-500 mg *Gymnema sylvestre* (Gumar)
10. 10-3,000 mg Arginine
11. 10-300 mg Green tea extract of Epigallocatechin gallate (EGCG)
12. 5-10,000 mg Butyrate
13. 1-200 mg *Mucuna puriens* (Cowage seed)
14. 10-1,200 mg Magnesium
15. 10-2,400 mg N-acetylcysteine (which can make Glutathione) and/or 25-3,000 mg Glutathione in any combination
16. 25-800 mg L-theanine
17. 10-750 mg *Magnolia officianalis*
18. 10-1,000 mg Taurine
19. 0.1-10 mg Melatonin
20. 10-300 mg Vitamin B-6
21. 10-10,000 mg Inositol
22. 1-30 mg Vinpocetin
23. 10-4,000 mg Glycine
24. 10-1,000 mg Niacinamide
25. 10-450 mg Valerian Root
26. 10-600 mg Kava kava
27. 10-500 mg Phosphatidylserine
28. 10-400 mg *Bacopa monnieri*
29. 10-600 mg *Rhodiola rosea*
30. 10-1,800 mg Holy basil
31. 10-2,000 mg Ashwagandha
32. 10-10,000 mg Vitamin C
33. 10-10,000 mcg Vitamin B-12
34. 10-9,000 mg Choline
35. 10-2,000 mg Methionine
36. 10-1,600 mg S-adenosylmethionine
37. 1-2,000 mg Calcium 38. 10-400 IU Vitamin E
39. 25-5,000 mcg Folate
40. 1-11 mg Manganese
41. 10-250 mg Vitamin B2
42. 10-25,000 IU Vitamin A
43. 25-800 mcg Selenium
44. 10-120 mg Zinc
45. 25-1,200 mg CoQ10
46. Carotenoid in the form of any of the following: 10-25,000 IU Alpha-carotene or Beta-carotene, 1-2 mg Beta-cryptoxanthin, 1-20 mg Zeaxanthin, 1-8 mg Lycopene or 1-40 mg Lutein
47. Bioflavonoid and/or any element that increases a Bioflavonoid including 10-750 mg Quercetin, 10-1,000 mg Hesperidin, 10-900 mg Garlic, and 10-360 mg Pycnogenol
48. 100-10,000 IU Vitamin D
49. 10-18,000 mg GABA The compound 10 can be administered orally in a pill, capsule, gelatine, powder, or liquid form twice per day two hours before or after a meal to maximize absorption thereof by the body. Alternative methods of administration could be intravenous, via suppository, transdermal patch, cream, gel, ointment, chewing gum, lozenge, and the like. Methods for delivering the compound 10 may utilize modified cellulase binders; hydroxypropyl methyl cellulose; liposomes; hypromellose materials for tablet binders, film coating, or as a matrix for the use in extended-release tablet formulations; nanotechnology delivery systems; hydrocolloids; and the like. For methods of delivery where the taste of the product is important, the compound 10 could be sweetened with sugar or low glycemic index sugar such as sucralose, stevia, agave nectar, xylitol, or the like.

Figure 4:
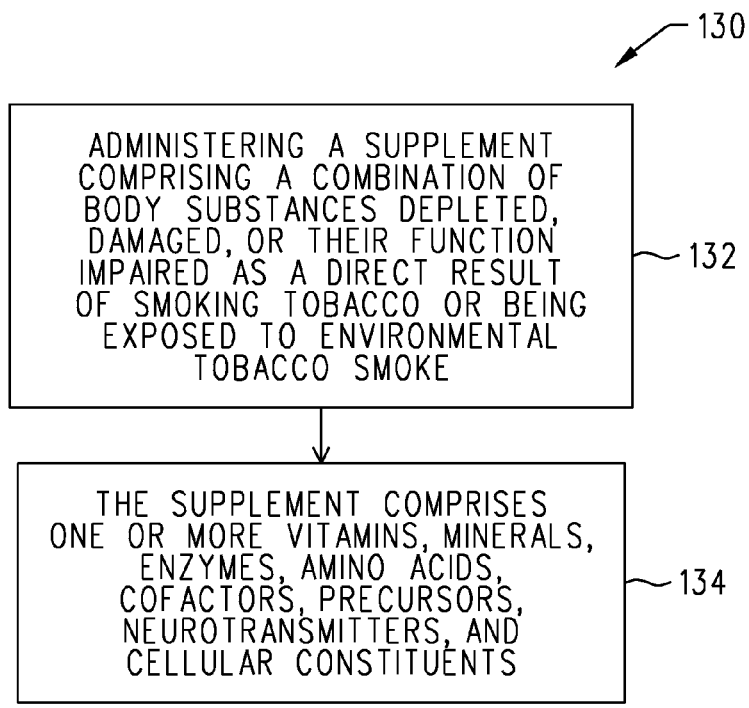
FIG. 4 is a schematic illustration of a method of replenishing body substances, repairing body substances, or ameliorating the function of body substances depleted, damaged or impaired in an individual as a direct result of smoking tobacco or being exposed to environmental tobacco smoke.

FIG. 4 schematically illustrates a method 130 of replenishing body substances, repairing body substances, or ameliorating the function of body substances depleted, damaged, or their function impaired as a direct result of smoking tobacco or being exposed to environmental tobacco smoke. The method 130 comprises a step 132 of administering a supplement 134 comprising a combination of body substances depleted, damaged or their function impaired in the individual as a direct result of smoking tobacco or being exposed to environmental tobacco smoke. The supplement 134 comprises one or more vitamins, minerals, enzymes, amino acids, cofactors, precursors, neurotransmitters, and cellular constituents. The supplement 134 replenishes, repairs, or ameliorates the function of multiple body substances depleted, damaged or their function impaired in the individual as a direct result of smoking tobacco or being exposed to environmental tobacco smoke. As described above with reference to FIG. 3, the supplement 134 may include nutrients that are depleted 26 from an individual's body as well as cellular constituents such as, for example, enzymes and cofactors that are depleted or damaged 28, FIG. 3, due to smoking tobacco or being exposed to environmental tobacco smoke. Nutrients that are depleted 26, FIG. 3, from an individual's body include (in any of their forms noted above) Vitamin B6, Biotin, Vitamin B12, Melatonin, Pantothenic acid, Dopamine, Serotonin, Choline (which maintains, reestablishes, and helps restore cellular membranes as described above), Calcium, Vitamin E, Folate, Magnesium, Manganese, Vitamin B2, Vitamin A, Vitamin C, Selenium, Zinc, Carotenoids, Bioflavonoids, Vitamin D, and Glutathione (which can be made from N-acetylcysteine). Cellular constituents that are depleted, damaged, or their function impaired 28 include vascular endothelium which can be improved by CoQ10 and Melatonin, Catalase which can be replenished by Bacopa, Glutathione reductase which can be replenished by N-acetyl-cysteine, Sulfhydryl moiety which is critical for enzyme function, Superoxide dismutase, and Peroxisomal enzyme (alkyl DHAP) which can be replenished by Butyrate.

Figure 5:
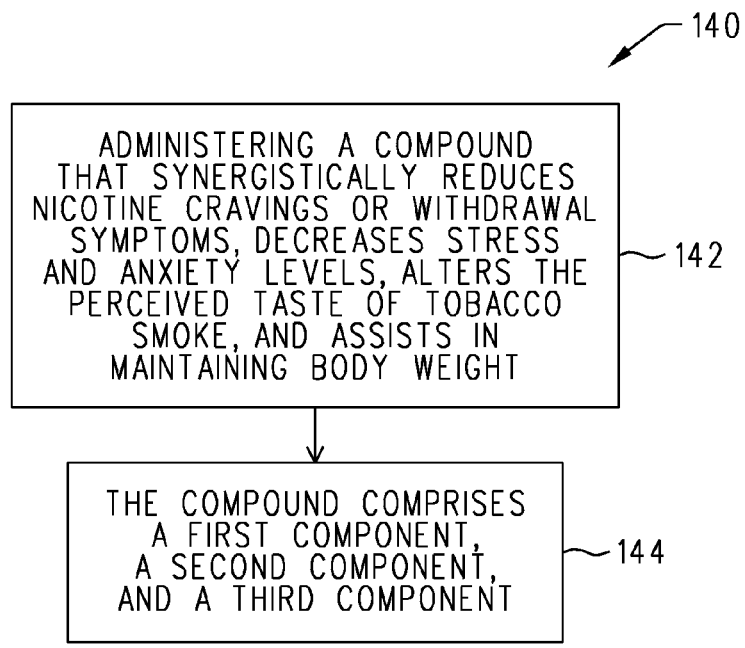
FIG. 5 is a schematic illustrating of a method of assisting an individual attempting to reduce or cease tobacco smoking.

FIG. 5 schematically illustrates a method 140 of assisting an individual attempting to reduce or cease tobacco smoking comprising the step 142 of administering a compound 144 that synergistically reduces nicotine cravings or withdrawal symptoms, decreases stress and anxiety, alters the perceived taste of tobacco smoke, and assists in maintaining body weight. The compound 144 comprises a first component 30, FIG. 1, comprising at least one element that blocks nicotine receptor sites in the individual. Such a first component 30 may be as described above relative to FIG. 1. The compound 144 also comprises a second component 40, FIG. 1, comprising at least one element that increases serotonin levels in the individual. Such a second component 40 may be as described above relative to FIG. 1. The compound 144 further comprises a third component 50, FIG. 1, comprising at least one body substance that has at least one of the above-described effects of replenishing at least one body substance depleted in the individual, repairing at least one body substance damaged in the individual, or ameliorating the function of at least one body substance impaired as a direct result of smoking tobacco.

Whereas the above description has been presented for purposes of illustration and description, it is not intended to be exhaustive or limit the concepts to the precise forms disclosed. Various other embodiments and modifications will be obvious to those skilled in the art after reading this disclosure, and it is intended that the appended claims be construed to cover such other embodiments and variations except insofar as limited by the prior art.

I claim:

1. A method of assisting an individual attempting to reduce or Cease tobacco smoking, consisting essentially of:
administering a compound that reduces nicotine cravings or withdrawal symptoms, decreases stress and anxiety, alters the perceived taste of tobacco smoke, and assists in maintaining body weight, the composition consisting essentially of:
a first component consisting essentially of at least one element that blocks nicotine receptor sites in the individual, wherein said first component comprises bivalent negative sulfur selected from a group consisting of hydropersulfides, alkyl sulfides, colloidal sulfur, organic thio compounds, thioglycols, and pharmaceutically acceptable thioglycol salts;
a second component consisting essentially of at least one element that increases serotonin levels in the individual, wherein the second component of the composition consists essentially of amino acids derived from tryptophan selected from a group consisting of 5-hydroxytryptophan and tryptophan derivatives or a serotonin receptor agonist; and
a third component consisting essentially of a combination of elements selected from the group consisting of Vitamin B6, Biotin, Vitamin B12, Melatonin, Choline, Calcium, Vitamin E, Folate, Magnesium, Manganese, Vitamin B2, Vitamin A, Vitamin C, Selenium, Zinc, a Carotenoid, Vitamin D, Glutathione, S-adenosylmethionine, CoQ10, N-acetylcysteine, and Superoxide dismutase.

2. The method of claim 1 wherein the supplement is administered orally in a pill, capsule, gelatine, powder, or liquid form, or is administered intravenously, via a suppository, transdermal patch, cream, gel, ointment, chewing gum or lozenge.

3. The method of claim 1 wherein the supplement is administered utilizing modified cellulase binders, hydroxypropyl methyl cellulose, liposomes, hypromellose materials for tablet binders, hypromellose materials for film coating, hypromellose materials as a matrix for the use in extended-release tablet formulations, nanotechnology delivery systems, or hydrocolloids.

4. The method of claim 1 wherein:
affecting the taste of tobacco smoke is accomplished by at least one of the first component, the second component, and the third component, or some combination thereof.

* * * * *